United States Patent [19]

Melnick et al.

[11] 3,986,927

[45] Oct. 19, 1976

[54] PROCESS FOR THE PURIFICATION AND STERILIZATION OF ACIDOPHILIC BIOLOGICALS BY EXTREME ACIDIFICATION AT COLD TEMPERATURES

[75] Inventors: Joseph L. Melnick; Craig Wallis, both of Houston, Tex.

[73] Assignee: Armour Pharmaceutical Company, Phoenix, Ariz.

[22] Filed: Apr. 28, 1975

[21] Appl. No.: 572,565

[52] U.S. Cl. ............................. 195/66 R; 195/1.7; 195/1.8; 195/124; 260/112 R; 536/9; 536/10; 536/15; 536/17; 260/559 AT; 21/58
[51] Int. Cl.² .................... C07G 7/02; C07G 7/026
[58] Field of Search ................ 195/65, 66 R, 66 A, 195/66 B, 118, 124; 260/112 R, 122, 210 E, 210 S, 559 AT; 21/58

[56] References Cited
UNITED STATES PATENTS

| | | | |
|---|---|---|---|
| 2,801,956 | 8/1957 | Baumgarten et al. | 195/66 R |
| 3,037,973 | 6/1962 | Sarcona | 260/559 AT X |
| 3,923,600 | 12/1975 | Yoshimura et al. | 195/66 R |

*Primary Examiner*—Lionel M. Shapiro
*Attorney, Agent, or Firm*—Richard R. Mybeck

[57] ABSTRACT

Methods of sterilizing biologicals in which the biologicals are acidified to a pH of not higher than about 1.0, preferably 0.75 to about 0.5, and the acidified biologicals are stored at cold temperatures for a perod of time sufficient to inactivate microbial flora contained therein but not the biological itself, for example, in the range of about 0° to about 10° C for 1–24 hours or longer. Precipitates formed during the storing are clarified and the biologicals are then neutralized, preferably to a pH of from about 7.0 to about 8.0, or that pH at which the biological is best stored, e.g., trypsin at pH 3–4. The methods include clarifying biologicals of precipitates formed within the first two to three hours and then continuing the storing and again clarifying the biologicals of precipitates.

Microbial flora and numerous contaminated proteins contained in the biologicals are removed resulting in completely sterilized biologicals retaining initial activity or titer. If desired, the clarified biologicals may be stored in acidic state since advantageously they reman biologically stable at ambient temperatures when stored at low pH levels, and then neutralized shortly before dispensing. A number of examples is set forth.

1 Claim, No Drawings

PROCESS FOR THE PURIFICATION AND STERILIZATION OF ACIDOPHILIC BIOLOGICALS BY EXTREME ACIDIFICATION AT COLD TEMPERATURES

BACKGROUND OF INVENTION

Biologicals heretofore have been subjected to filtration for the purpose of sterilization. However, filtration does not always remove small bacteria, nor will bacteriological filters retain mycoplasma, or viruses. Fedoroff, S., Evans, V. J., Hopps, H. E., Sanford, K. K. and Boone, C. W. Summary of proceedings of a workshop on serum for tissue culture purposes. In Vitro: Vol. 7, 1972, p. 161–167. Barile, M. F. and Kern, J. Isolation of *Mycoplasma arginini* from commercial bovine sera and its implication in contaminated cell cultures. Proc. Soc. Exp. Biol. & Med. Vol. 138, 1971, p. 432–437.

For example, the sterilization of trypsin for use in digestion of mammalian tissues and tissue and cell cultures and for other purposes or the sterilization of other biologicals poses a serious problem. For instance, and as set forth in the foregoing publications, trypsin used to disperse secondary, continuous normal and continuous transformed tissue and cell cultures or other biologicals cannot be efficiently sterilized by conventional filtration through 0.22 micron filters. Further, as set forth in the foregoing publications, such bacteriological filtrates often contain adventitious viruses, mycoplasma and minute forms of pseudomonas and other bacteria which pass defective membrane pores. The presence of these contaminants poses a serious problem in all types of biological research and development requiring sterile or non-contaminated biological fluids.

In addition to the above problems, the repeated filtration of trypsin or other enzymes during the processes of clarification often allows the enzyme to autolyze, adding even more materially to the cost of the product, and the prolonged period of time required to clarify trypsin or other biologicals at ambient temperatures allows bacteria present therein to synthesize a variety of toxins which are then collected in the filtrate since they are smaller than the pores of filters used for sterilization. Even though bacterially sterile by filtration, biologicals that once contained bacteria may be spoiled for their original purposes because the product has now become cytotoxic and pyrogenic, and also may and often does contain agents which pass the filter, e.g., viruses and mycoplasma, as set forth in the foregoing publications.

Although acidic pH levels have been shown in the past to inactivate a variety of microorganisms, such application for biologics, i.e., human serum products, enzymes, hormones, antibiotics and other biologic fluids, etc., has never been successful or made feasible for sterilization of such fluids in the past. The parameters for complete sterilization of bacteria, viruses, spores, fungi and molds, yeast, mycoplasma, and other microbial flora previously have not been attained. In addition, the effects of acidic pH levels as ordinarily applied in the past fail to inactivate the very resistant aerobic and anaerobic spore-forming bacterium.

It would be highly advantageous to provide and the present invention is directed to a process of purifying and sterilizing biologicals without deleteriously affecting the biological, e.g., the proteolytic activity of the enzymes, by a relatively simple and inexpensive process in which the biological is acidified to a pH of not over about 1.0 and the acidified biological is stored at temperatures and for periods of time sufficient to inactivate the microbial flora without deleteriously affecting the biological or its proteolytic activity.

SUMMARY

The present invention is directed to the discovery of methods by which biological fluids and products can be successfully sterilized and purified without denaturing the product, or deleteriously affecting the cell culture or the host being administered the product. More specifically, the present invention resides in the discovery that certain biologicals can be purified and that microbiological flora, i.e., viruses, mycoplasma, bacterium, yeast, fungi, and molds, present in the biologicals, may be specifically inactivated without deleteriously affecting the biological, e.g., the proteolytic activity of the enzymes.

In general, we have discovered that by increasing the hydrogen ions in the biological and decreasing the temperature of certain biologics, as described later in this specification, complete sterilization occurs by inactivating viruses, bacterium, spores, fungi and molds, yeast, mycoplasma, and other microbial flora. The acidification of the biological to a pH of not higher than about 1.0 at temperatures from about 0° to about 10° C for prolonged periods of time at pH 1.0–0.5 renders the microbiological flora inactive. After only a few minutes at pH 1.0–0.5, all viruses, mycoplasma and other microbiological flora in the biological are inactivated, but spore-forming bacteria remain viable. After prolonged treatment at pH 1.0–0.5 at 0° to 10° C, and preferably 4° C are all spores inactivated. At pH 1.0 (±0.2) inactivation of viruses takes place in ½ to 1 hour. Unexpectedly, the prolonged incubation of these biologicals, for example, trypsin, at pH 1.0–0.5 at 4° C or other cold temperatures up to about 10° C does not affect the proteolytic activity of the enzyme, and this treatment precipitates the major portion of contaminating proteins from the enzyme solution, which can readily be removed by clarification, leaving a sterile and relatively pure enzyme product of unimpaired proteolytic activity.

It is therefore an object of the present invention to provide a process for the purification and sterilization of biologicals resistant to extreme acidification.

It is a further object of the present invention to provide a process of eliminating extraneous microorganisms present in biologicals by selectively inactivating adventitious or contaminating viruses, bacterium, spores, fungi, molds, yeast, mycoplasma, and other microbial flora present therein by acidifying the biological to a pH level of 1.0 or less for different periods of time and at cold temperatures to stabilize the biological under test.

Yet a further object of the present invention is the provision of a process of eliminating microbial flora present in biologicals by selectively inactivating adventitious or contaminating viruses, bacterium, spores, fungi, molds, yeast, mycoplasma, and other microbial flora present therein by acidifying the biological to a pH level of not higher than about 1.0, holding it at elevated temperatures in the range of about 0° to about 10° C for periods of time sufficient to inactivate such microbial flora, and in which the major portion of contaminating proteins are precipitated and clarified from the solution, leaving a sterile biologic, and, in the case of enzymes, a relatively pure and sterile enzyme product of unimpaired proteolytic activity.

A further object of the present invention is the provision of such a process of sterilizing biologicals in which the biological may be stored at the pH level of 1.0 or less for extended periods of time and at ambient or cold temperatures, if desired, and which subsequently may be neutralized and aseptically dispensed.

A further object of the present invention is the provision of such a process of sterilization and purification of biologicals in which the activity of proteolytic enzymes is unaffected and by which a sterile and relatively pure enzyme product is obtained.

Yet a further object of the present invention is the provision of such a process which effectively sterilizes and purifies the biological without loss of activity and which is relatively simple and inexpensive.

Other and further objects, features and advantages of the invention will appear from the following description of presently-preferred embodiments, from the foregoing abstract of the disclosure, the background of the invention, and from the claims.

DESCRIPTION OF PRESENTLY-PREFERRED EMBODIMENTS

Biologicals are solubilized or suspended in a liquid carrier and acidified to a pH level of not higher than about 1.0, and preferably 0.75 to 0.5, lower limits being operable but the lower limit of 0.75 being for the purpose of convenience, practicality and economics. The acidified biological is then held or stored for a period of time, preferably at cold temperatures in the range of from about 0° to about 10° C, with 4° C being preferred. The period of storing should be for a time sufficient to inactivate all extraneous microorganisms present in the biological. For most biologicals from about 18–24 hours at 4° C is sufficient at pH 0.75 to 1.0 or pH 0.5 for shorter periods of time.

With some biologicals, for example, trypsin, during the first 3–5 hours of incubation, a precipitate is formed which might entrap spore-forming organisms and protect them against the bactericidal effects of the acid. In these cases, the suspension is clarified at this time through a coarse filter of 1–20 micron porosity to remove these precipitates, and the clarified trypsin is then held at these temperatures for the remainder of the 18–25 hours or longer, if desired. The biological, such as trypsin, is then aseptically passed through a sterile clarifying pad of 1–5 micron porosity to remove those contaminants which were precipitated during the remainder of the holding period, and the clear filtrate is then neutralized before use. If desired, the acidified filtrate may be stored at ambient temperatures, and then neutralized shortly before use. After neutralization, the filtrate is stored at temperatures from −20° to −90° C prior to use.

As used herein, the term "biologicals" means enzymes, hormones, serum proteins and antibiotics, such as trypsin, streptomycin, nystatin, gamma globulin, enzymes, hormones, antibiotics and other biologic fluids resistant to extreme acidification.

Among the acids which may be used to acidify the biologicals are hydrochloric, sulfuric, sulfurous, oxalic and nitric acids.

Basic substances which may be used to neutralize the acid-treated biologicals include sodium hydroxide; sodium carbonate; sodium carbonate, acid; potassium hydroxide; potassium carbonate; potassium carbonate, acid; and the like.

Preferably, the biologicals are solubilized or suspended in water, but other liquid carriers may be used, such as saline or carbohydrate solutions. The term "biological in a liquid carrier" as used herein means that the biological is suspended or dissolved in a suitable liquid.

The temperature range of treatment may range from about 0° to 10° C. Temperatures above this range may not be used since it may destroy the biological.

The time of treatment should be for a period sufficiently long to inactivate the extraneous microorganisms present which include adventitious or contaminating viruses, bacterium, spores, fungi, molds, yeast, mycoplasma and other microbial flora. After only a few minutes at pH 1.0–0.5, all viruses, mycoplasma and other microbiological flora are inactivated, but spore-forming bacteria remain viable. Only at prolonged treatment at a pH level of 1.0 or below, preferably 0.5–0.75, are all spores inactivated. Normally, a period of from about 18–25 hours at 4° C will inactivate all spores at pH 1.0 to 0.75 or pH 0.5 for shorter periods of time at temperatures up to about 10° C.

In those biologicals which form precipitates during the early stages of incubation, the precipitate is clarified at this time through a coarse filter of 1–20 micron porosity to remove these precipitates as they might entrap spore-forming organisms that protect them against the bactericidal effects of the acid. The clarified biological is then stored at the desired temperature for the remainder of the period of time. At the end of this period of time the acidified biological is aseptically passed through a sterile clarifying pad of 1–5 micron porosity to remove those contaminants which were precipitated after initial clarification and the clear filtrate may then be dispensed as previously described.

The resulting biological is completely sterilized and is relatively pure without deleteriously affecting the proteolytic activity of the biological.

All the biologicals subject to treatment by the process of this invention are well known, and standard methods are available for measuring their potency, which is normally set forth as the titer. The methods used for measuring the potency of the biologicals referred to in this specification and in the following examples and tables are described in standard tests as set forth in the following publications. These tests for activity or titer are in widespread use and injection into humans or animals is no longer done to determine potency since the in vitro tests are much more precise, as for example measuring poliovirus neutralizing antibody titers of human gamma globulin in cell culture rather than in animals. Opton, E. M., Nagaki, D. and Melnick, J. L.: Poliomyelitis antibodies in human gamma globulin. J. Immunol. Vol. 75, 1955, p. 178–185. Other tests include (a) antibiotics and antimycotics by the standard antibiotic or antimycotic sensitivity test using a sensitive test organism. Lorian, V. Antibiotics and Chemotherapeutic Agents in Clinical and Laboratory Practice. Charles C. Thomas Publ., Springfield, Ill., 1966; (b) total protein by the Lowry method. Lowry, O. H., Rosebrough, N. J., Farr, A. L. and Randall, R. J.: Protein measurement with the Folin phenol reagent. J. Biol. Chem. Vol. 193, 1951, p. 265–275; (c) proteolytic titer of enzymes as described in detail by Wallis, Ver, and Melnick. Wallis, C., Ver, B. and Melnick, J. L.: The role of serum and fetuin in the growth of monkey kidney cells in culture. Exp. Cell Research, Vol. 58, 1969, p. 271–282; and (d) antigenetic titer as described in detail by Wallis and Melnick: Detection of protein contaminants in biological preparations by discontinuous counterimmunoelectrophoresis. Infection and Immunity, Vol. 6, 1972, p. 557–560.

The following examples are given to illustrate embodiments of our invention, many variations of which are possible without departing from its spirit or scope.

EXAMPLE I

A 10% suspension of trypsin was made by adding 10 grams of powdered trypsin to a beaker and a quantity of water sufficient to make 100 ml. The suspension was vigorously mixed by magnetic stirring for 5–10 minutes at ambient temperatures, which solubilized the proteolytic enzyme. The solution was then passed through a coarse filter (1–20 micron porosity) to remove nonsolubilized, contaminating products and the filtrate containing all the proteolytic activity was then adjusted to a pH of 0.75 by adding a sufficient quantity of hydrochloric acid.

The trypsin solution was then placed in a sterile container and held at 4° C for 18 hours. During the first 3–5 hours of incubation, a precipitate formed which might entrap spore-forming organisms and protect them against the bactericidal effects of the acid. Therefore, the suspension was clarified at this time through a coarse filter (1–5 micron porosity) to remove these precipitates, and the clarified trypsin was then stored at 4° C for the remainder of a period of time from 18–24 hours. The trypsin held at pH 0.75 at 4° C for 18–24 hours was then aseptically passed through a sterile clarifying pad to remove those contaminants which were precipitated during the remainder of the period of time, and the clear filtrate was dispensed in bottles or ampules and stored at −20° to −90° C prior to use.

The total protein of the trypsin solution when initially solubilized was 90 mg/ml and the proteolytic titer 1:1280 (the highest dilution of the solution which cleared 4 mg casein in 1 hour at 37° C). After solubilization and removal of the solids from the crude solution the total protein was 60 mg/ml and the proteolytic titer remained the same as above. After acidification to pH 0.75 and storage at 4° C for 18 hours, the sterile clarified enzyme solution only contained 34 mg/ml protein, of which 22 mg/ml contained the enzymatic activity and still retained the initial proteolytic titer of 1:1280.

Since the 10% trypsin solution was about 50 times more concentrated than is conventionally used for treatment of cell cultures or organs, a portion of the pH 0.75 sterile trypsin was diluted about 50-fold in a salt solution for use. A base, i.e., NaOH or NaHCO$_3$, was added to the dilute trypsin solution to attain a pH of 7.0–8.0, for optimal activity of the enzyme.

A portion of the product sterilized at pH 0.75 was adjusted to pH 3.0 and stored at that pH and examined for stability after storage at −40°, 4°, 25° and 37° C. In addition to the sterilization of trypsin by the method described, its storability at acid pH levels proved to be complete, without detectable inactivation of the proteolytic activity, which thus facilitates the storage and shipment of this product at ambient temperatures. In the case of presently available trypsin conventionally processed by filtration, rapid inactivation occurs when stored at ambient temperatures.

The following Table I indicates the rapidity of solubilization of trypsin and the effects of rapid solubilization on trypsin activity.

TABLE I

Effects of Rapid Solubilization on Trypsin Activity

| Minutes Stirred[a] | Proteolytic Titer[b] | mg/ml Protein |
|---|---|---|
| 10 Seconds | 1280 | 85 |
| 10 | 1280 | 90 |
| 20 | 1280 | 91 |
| 40 | 1280 | 95 |
| 80 | 1280 | 95 |
| 160 | 1280 | 97 |

[a] 4 grams of powdered commercial trypsin were added to 36 ml distilled water, and the suspension was vigorously stirred on a magnetic unit without mechanical foaming. After addition of the powder (10 seconds), a 3 ml sample was obtained, immediately filtered through coarse filter paper to remove insolubilized powder, and the clear filtrate was assayed for proteolytic activity and total protein. Representative samples were also obtained at the intervals indicated and processed as described.
[b] Reciprocal of the highest dilution which cleared skim milk.

EXAMPLE II

In this example, the trypsin solution of Example I was acidified to different pH levels and held for 19 hours at a temperature of 4° C with results, all as set forth in the following Table II:

TABLE II

Effect of Different pH Levels on Trypsin

| Trypsin Acidified at pH | Hours of Treatment at 37° C | Proteolytic Titer (Reciprocal) | Bacterial Counts (Per 0.1 ml) |
|---|---|---|---|
| 4.4 (Control) | 0 | 1280 | 1000 |
|  | 19 | 1280 | 10000 |
| 3.5 | 0 | 1280 | 10000 |
|  | 19 | 1280 | 10000 |
| 2.5 | 0 | 1280 | 10000 |
|  | 19 | 1280 | 2000 |
| 1.0 | 0 | 1280 | 3000 |
|  | 19 | 1280 | 0 |
| 0.75 | 0 | 1280 | 200 |
|  | 19 | 1280 | 0 |
| 0.5 | 0 | 1280 | 14 |
|  | 19 | 1280 | 0 |

EXAMPLE III

This example illustrates the selective purification of raw, commercial trypsin, as described under Example I.

10 grams of commercial swine trypsin, in this case obtained from Difco Laboratories, Detroit, Mich., was suspended in distilled water to make a 10% suspension, a final volume of 100 ml, and the pH derived from this solubilization of trypsin was about 4.6. While magnetically stirring the suspension, 1 to 12 N HCl acid was added to attain a pH of 0.75. The massive precipitate in the solution was then removed by passing the trypsin solution through a series of coarse filters, or removed by centrifugation. During the first 3–5 hours of incubation at 4° C, a precipitate formed which might entrap spore-forming organisms and protect them against the bactericidal effects of the acid. Therefore, the suspension was clarified at this time through a coarse filter (1–20 micron porosity) to remove the precipitate, and the clarified trypsin was then stored as described supra, 4° C for a total of 18–24 hours. The clarified filtrate was then placed in a sterile dispensing jar, and held at about 4° C for 18 hours. The resulting precipitate which formed was removed by passing the trypsin solution aseptically through a coarse fibreglass pad, and then the resultant clear filtrate was aseptically adjusted to pH 3.0 and dispensed into vials and stored at −20° to −90° C. The proteolytic titer of the trypsin when initially solubilized was 1:1280, and the final product as dispensed for storage also had a titer of 1:1280. The total protein initially at the time of solubilization of the trypsin was 90 mg/ml, and the final product had 34 mg/ml, indicating a significant purification of the enzyme preparation.

The control, untreated trypsin, and the trypsin purified and sterilized at pH 0.75 were electrophoresed on cellulose acetate strips and stained with Ponceau S, and then the strips were scanned on a Beckman Microzone densitometer. Darkened bands in the tracings of electrophoresis strips from the sterilized trypsin indicated the proteolytic activity. Approximately 87% of the proteins other than trypsin were removed and the remaining proteins were approximately 65% trypsin.

The following Table III illustrates the degree of purification attained with this process.

TABLE III

Flow Chart - Total Protein Contents (Column 1) and Enzymatic Proteins (i.e., Proteins with Proteolytic Activity) (Column 2)

| | Column 1 | Column 2 | Column 3 |
|---|---|---|---|
| | mg/ml of Total Protein | mg/ml of Active Enzymatic Proteins | Proteolytic Titer |
| 10% Raw Trypsin Solubilized at pH 4.4 in Water | 90 | 22 | 1280 |
| After Coarse Clarification of Above | 87 | 22 | 1280 |
| Acidification at pH 0.75 | 60 | 22 | 1280 |
| Clarification of Solution at pH 0.75 | 60 | 22 | 1280 |
| After 18-19 Hours at pH 0.75, 4° | 34 | 18 | 1280 |
| After Coarse Clarification of Above | 24 | 18 | 1280 |

Although total protein (Column 1) is reduced in the final preparation, the enzymatic proteins (Column 2) and the enzymatic activity (titer) (Column 3) remain the same. Thus, purification was achieved.

Such trypsin can be readily used by thawing the frozen ampule and diluting the trypsin 1:50 in phosphate-buffered saline. Since trypsin is more active in the basic pH ranges, the trypsin solution was treated with a base, NaOH or NaHCO$_3$, until the solution attained a pH of about 7.5.

EXAMPLE IV

A 10% suspension of trypsin was made by adding 10 grams of powdered trypsin to a beaker and a quantity of water sufficient to make 100 ml. The suspension was vigorously mixed by magnetic stirring for 5–10 minutes at ambient temperatures, which solubilized the proteolytic enzyme. The solution was then passed through a coarse filter (1–20 micron porosity) to remove non-solubilized, contaminating products and the filtrate containing all the proteolytic activity was then adjusted to a pH of 0.5 by adding a sufficient quantity of hydrochloric acid.

The trypsin solution was then placed in a sterile container and held at 0° C for 1 hour. During the first ½ hour of incubation, a precipitate formed which might entrap spore-forming organisms and protect them against the bactericidal effects of the acid. Therefore, the suspension was clarified at this time through a coarse filter (1–5 micron porosity) to remove these precipitates, and the clarified trypsin was then stored at 0° C for the remaining ½ hour. The trypsin held at pH 0.5 at 0° C for 1 hour was then aseptically passed through a sterile clarifying pad to remove those contaminants which were precipitated during the remainder of the period of time, and the clear filtrate was adjusted to pH 3.0 and dispensed in bottles or ampules and stored at −20° to −90° C prior to use.

The total protein of the trypsin solution when initially solubilized was 90 mg/ml and the proteolytic titer 1:1280 (the highest dilution of the solution which cleared 4 mg casein in 1 hour at 37° C). After solubilization and removal of the solids from the crude solution the total protein was 60 mg/ml and the proteolytic titer remained the same as above. After acidification to pH 0.5 and storage at 0° C for 1 hour, the sterile clarified enzyme solution only contained 42 mg/ml protein, of which 22 mg/ml contained the enzymatic activity and still retained the initial proteolytic titer of 1:1280.

Since the 10% trypsin solution was about 50 times more concentrated than is conventionally used for treatment of cell cultures or organs, a portion of the pH 0.5 sterile trypsin was diluted about 50-fold in a salt solution for use. A base, i.e., NaOH or NaHCO$_3$, was added to the dilute trypsin solution to attain a pH of 7.0–8.0, for optimal activity of the enzyme.

A portion of the product sterilized at pH 0.5 was stored at pH 3.0 and examined for stability after storage at −40°, 4°, 25° and 37° C. In addition to the sterilization of trypsin by the method described, its storability at pH 3.0 proved to be complete, without detectable inactivation of the proteolytic activity, which thus facilitates the storage and shipment of this product at ambient temperatures. In the case of presently available trypsin conventionally processed by filtration, rapid inactivation occurs when stored at ambient temperatures.

EXAMPLE V

Although the foregoing examples illustrate desirable parameters for sterilization and purification of trypsin, many other variations can be used with the same effects. Other percentages of trypsin can be made in the diluent. At pH of 1.0 to about 0.5 trypsin is purified by storage for 18 hours at 4° C and by storage for about 1 hour at pH 0.5. However, lower or higher temperatures can be used to the same extent, and thus longer or shorter storage times are required, e.g., 10° C storage for about 36–48 hours, and at 0° C for about 1 hour and the like.

EXAMPLE VI

This example illustrates the selective inactivation of a variety of natural bacteria, viruses, mycoplasma, yeast and molds present in most raw, commercial trypsin by the present invention.

The trypsin solubilized as described in Example III was treated with the following organisms per ml: 350,000 assorted aerobic bacteria, 6,500 assorted facultative aerobic bacteria, 800 yeast (Candida albicans), 2,500 molds, 600 plaque forming units (PFU) of swine enteroviruses, 2,000 PFU of poliovirus, 3,500 swine mycoplasma, 2,000 aerobic spore-forming bacteria and 2,700 anaerobic spore-forming bacteria. After acidification of the trypsin to pH 0.75 as described in Example III, and clarification, the trypsin was re-assayed for the total microbiological flora (about 30 minutes of initial solubilization), and only the spore-forming bacterium were detectable but no inactivation of the trypsin was evident. However, after 18 hours at 4° C at pH 0.75, no detectable colonies were evident when samples were plated under anaerobic conditions, nor were there any colonies on medium plated to detect and quantify the areobic spore-formers. Thus, complete sterilization was attained by the treatment described in Example III without any loss of enzymatic activity.

EXAMPLE VII

This example shows the selective sterilization of chymotrypsin, papain and pancreatin.

These enzymes were solubilized in water as described for trypsin in Example III, treated with the same microbiological flora as described in Example VI, acidified to pH 0.75 and held at 4° C for 18 hours. No detectable decrease in proteolytic titer occurred in any of the enzymes processed.

Contaminating microbiological flora present in these preparations were no longer detectable after the sterilization process.

EXAMPLE VIII

This example illustrates the selective sterilization of streptomycin, in the form of dihydrostreptomycin sulfate.

25 grams of streptomycin obtained from Pfizer was solubilized with 75 ml of distilled water and treated with the same microbiological flora as described in Example VI. The pH of the solution (about 5.6) was adjusted to 0.75 with HCl, and the antibiotic was stored overnight at 4° C (22 hours). The antibiotic activity of the sterilized streptomycin was then tested against a sensitive bacterium and found to have retained its full activity as compared to freshly prepared streptomycin, using the test procedure described in the Article by Lorain, V., set forth earlier. After the sterilization process, no microbiological flora were detected after plating or assaying, indicating complete sterility.

EXAMPLE IX

This example illustrates the selective sterilization of a variety of other antibiotics, including gentamycin, kanomycin, erythromycin, and tetracycline.

The above antibiotics were contaminated with the same microbiological flora as described in Example VI. After solubilization and processing of these antibiotics as described in Example VIII for streptomycin, full activity of all antibiotics was retained as evidenced by assay of the antibiotics against a sensitive test organism. After the sterilization process, no microbiological flora were detected after plating or assaying, indicating complete sterility.

EXAMPLE X

This example illustrates the selective sterilization of nystatin in the form of nystatin sulfate.

25 grams of nystatin obtained from Squibb Pharmaceutical was suspended in 75 ml distilled water and treated with the same microbiological flora as described in Example VI. The pH of the solution (about 5.5) was adjusted to 0.75 with HCl, and the antimycotic was stored overnight at 4° C (22 hours). The antimycotic activity of the sterilized nystatin was then tested against a sensitive fungi — Candida albicans — and found to have retained its full activity as compared to freshly prepared nystatin. After the sterilization process, no microbiological flora were detected after plating or assaying, indicating complete sterility.

EXAMPLE XI

In this example, the biologicals of the preceding examples are acidified with sulfuric, sulfurous, oxalic and nitric acids and are treated as described. The biologicals are suspended or dissolved in water, saline or carbohydrate solutions. The pH levels are adjusted from about 1.0 to 0.5 and the biologicals are held at temperatures from about 4° to about 10° C for periods of 1 hour up to 18–24 hours and longer. There are no deleterious effects by storing the acidified biological for longer than 24 hours, and the product can be stored at the treating pH level at cold temperatures for long periods of time without any deleterious effects.

All of the treated biologicals in this Example XI are neutralized to a pH between 7–8 with sodium hydroxide, sodium carbonate, sodium carbonate (acid), potassium hydroxide, and potassium carbonate (acid) and may then be used, however, after being neutralized, the purified and sterilized biological should be frozen and preferably stored at temperatures of −20° to −90° C, and then thawed before use.

The present invention accomplished sterilization and purification of biologicals without loss of activity by a relatively simple and inexpensive process.

All biologicals resistant to extreme acidification are effectively sterilized and purified by the process of the present invention without loss in proteolytic titer or other activity.

The present invention, therefore, is well suited and adapted to attain the objects and has the advantages mentioned as well as other inherent therein.

While numerous examples of the invention have been given for purposes of disclosures, changes in parameters and details may be made which are within the spirit of the invention as defined by the scope of the appended claims.

What is claimed is:

1. A method of sterilizing trypsin, including acidifying trypsin to a pH of not higher than about 1.0, storing the acidified trypsin at a temperature of from about 0° to about 10° C for a period of time sufficient to inactivate microbial flora disposed therein without inactivating the trypsin, clarifying the stored trypsin to remove therefrom precipitates formed therewithin during the first half hour of said period, continuing said storing for the remainder of said period, reclarifying the said trypsin to remove therefrom all precipitates formed therewithin during the remainder of said period, and neutralizing the reclarified trypsin to a pH of from about 7.0 to about 8.0.

* * * * *